United States Patent [19]

Murphy et al.

[11] 4,144,395

[45] Mar. 13, 1979

[54] PROCESS FOR THE PREPARATION OF POLYETHER-ESTER POLYOLS

[75] Inventors: John R. Murphy; Louis C. Pizzini, both of Trenton, Mich.

[73] Assignee: BASF Wyandotte Corporation, Wyandotte, Mich.

[21] Appl. No.: 857,072

[22] Filed: Dec. 5, 1977

[51] Int. Cl.² ............................................. C07C 69/60
[52] U.S. Cl. .................................... 560/200; 560/83; 560/91; 560/93; 560/119; 560/120; 560/127
[58] Field of Search ................... 560/79, 91, 182, 198, 560/209, 200

[56] References Cited

U.S. PATENT DOCUMENTS

| | | | |
|---|---|---|---|
| 3,459,733 | 8/1969 | Byrd, Jr. et al. | 536/4 |
| 3,585,185 | 6/1971 | Levis, Jr. et al. | 536/4 |
| 3,676,398 | 7/1972 | D'Alelio | 560/209 |
| 3,770,602 | 2/1972 | D'Alelio | 560/198 |

Primary Examiner—James O. Thomas, Jr.
Assistant Examiner—Leah Hendriksen
Attorney, Agent, or Firm—Joseph D. Michaels; Bernhard R. Swick; Robert E. Dunn

[57] ABSTRACT

Polyether-ester polyols are prepared in the presence of from 0.005 percent to 0.01 percent by weight (50-100 ppm) of a trialkylamine. The resulting polyols have improved color and are obtained in markedly reduced reaction times.

6 Claims, No Drawings

PROCESS FOR THE PREPARATION OF POLYETHER-ESTER POLYOLS

BACKGROUND OF THE INVENTION

1. Field of the Invention

The present invention relates to a process for the preparation of polyether-ester polyols. More particularly, the invention relates to the preparation of these polyols employing certain alkylamines as catalysts therefor.

2. Prior Art

The preparation of polyether-ester polyols by the reaction of an alkylene oxide with a half-acid ester obtained by the reaction of a polyol with an unsaturated polycarboxylic acid anhydride is well known in the art as evidenced by inter alia U.S. Pat. Nos. 3,459,733; 3,585,185; 3,639,541 and 3,639,542. The latter three patents also teach that trialkylamines may be employed as catalysts for the reaction in amounts ranging from 0.2 percent to 2.5 percent by weight based on the weight of the starting polyol. However, use of these amounts of trialkylamines results in products having poor color quality affecting their utility as reactants in the preparation of polyurethane foams. Accordingly, it is conventional in the art to prepare polyether-ester polyols either in the absence of catalysts or in the presence of inorganic alkaline catalysts. Both alternatives create problems, the former requiring almost twice the reaction time while the latter involves difficult and costly catalyst removal operations.

SUMMARY OF THE INVENTION

The present invention is directed to an improvement in the process for the preparation of polyether-ester polyols comprising employing as catalysts therefor very low levels of trialkylamine, i.e., from 50 to 100 parts per million based on the weight of the starting polyol. Surprisingly, it has been found that at these low levels trialkylamines can be effectively employed as catalysts. The resulting products are light in color and are prepared in relatively quick reaction periods.

DESCRIPTION OF THE PREFERRED EMBODIMENTS

The trialkylamines which are employed in the process of the subject invention are those amines having from 2 to 4 carbon atoms in the alkyl chain. They include triethylamine, tri-n-propylamine, tri-isopropylamine, tri-n-butylamine, and tri-isobutylamine, and tri-p-butylamine. As mentioned above, only low levels of these amines may be employed efficiently in the process of the subject invention. The amounts of amines which may be employed vary from 50 to 100 parts per million based on the weight of the starting polyol.

There are three reactants which are employed in the preparation of the polyether-ester polyols of the subject invention, namely, an alkylene oxide, a polyether polyol and a polycarboxylic acid anhydride.

Alkylene oxides which may be employed in the preparation of the polyols of the present invention include ethylene oxide, propylene oxide, the isomeric normal butylene oxides, hexylene oxide, octylene oxide, dodecene oxide, methoxy and other alkoxy propylene oxides, styrene oxide, and cyclohexene oxide. Halogenated alkylene oxides may also be used, such as epichlorohydrin, epiiodohydrin, epibromohydrin, 3,3-dichloropropylene oxide, 3-chloro-1,2-epoxypropane, 3-chloro-1,2-epoxybutane, 1-chloro-2,3-epoxybutane, 3,4-dichloro-1,2-epoxybutane, 1,4-dichloro-2,3-epoxybutane, 1-chloro-2,3-epoxybutane, and 3,3,3-trichloropropylene oxide. Mixtures of any above alkylene oxides may also be employed.

The polycarboxylic acid anhydrides which may be employed in the present invention include: maleic anhydride, fumaric anhydride, propenosuccinic anhydride, and various halogenated anhydrides such as: dichloromaleic anhydride, tetrabromophthalic anhydride, tetrachlorophthalic anhydride, 1,4,5,6,7,7-hexachlorobicyclo(2,2,1)-5-heptane-2-dicarboxylic anhydride, hereinafter called chlorendic anhydride, 1,4,5,6,7,7-hexachloro-2-methylbicyclo(2,2,1)-5-heptene-2,3-dicarboxylic anhydride, 1,4,5,6,7,7-hexachlorobicyclo(2,2,1)-5-heptene-2-acetic-2-carboxylic anhydride, 5,6,7,8,9,9-hexachloro-1,2,3,4,4a,5,-8,8a-octahydro-5,8-methano-2,3-naphthalene, dicarboxylic anhydride, and 1,2,3,4,5,6,7,7-octachloro-3,6-methano-1,2,-3,6-tetrahydrophthalic anhydride. Mixtures of any of the above anhydrides may also be employed.

The polyether polyols which are employed in the subject invention are well known in the art and are generally referred to as polyoxyalkylene ether polyols. These polyols are prepared by the reaction of an alkylene oxide with a polyhydric alcohol. Any of the alkylene oxides referred to above may be employed in the preparation of the polyols used in the subject invention. The polyalkylene polyether polyols may have either primary or secondary hydroxyl groups and preferably are polyethers prepared from alkylene oxides having from 2 to 6 carbon atoms such as polyethylene and polypropylene ether polyols. The polyalkylene polyether polyols may be prepared by any known process such as, for example, the process disclosed by Wurtz in 1859 and Encyclopedia of Chemical Technology, Vol. 7, pages 257–262 published by Interscience Publishers, Inc. (1951) or in U.S. Pat. No. 1,922,459.

Polyhydric alcohols which may be reacted with the alkylene oxides to prepare the polyalkylene ether polyols employed in the subject invention include ethylene glycol, propylene glycol, the isomeric butylene glycols, 1,5-pentane diol, 1,6-hexane diol, glycerol, trimethylolpropane, 1,2,6-hexane triol, pentaerythritol, sorbitol, sucrose and α-methyl glycoside. In addition to polyhydric alcohols other organic compounds having at least two reactive hydrogen atoms may be employed in the preparation of the polyols used in the subject invention. These compounds include amines such as alkylamines, alkylene polyamines, toluenediamine; phenol compounds such as bisphenol, resorcinol; mercaptans, acid amides and acids of phosphorous, such as those having a $P_2O_5$ equivalency of from about 72 percent to about 95 percent, preferably the phosphoric acids. Generally the polyols will have a molecular weight between 500 and 10,000, preferably between 500 and 6000.

The polyether-ester polyols are generally prepared by heating the reactants at temperatures between 50° C. and 150° C., preferably between 75° C. to 150° C., for 0.5 to 10 hours. Temperatures below 150° C. must be maintained to prevent the reaction of carboxy and hydroxy groups with the formation of water. The reaction is generally carried out under from 0 to 100 psig. Alternatively, the alkylene oxide condensates and the polycarboxylic acid anhydride may be added to a reaction vessel and heated to 50° C. to 150° C. for zero to ten hours. Thereafter, the alkylene oxide is added to the reaction mixture under pressure while maintaining the reaction temperature of between 75° C. and 150° C. After completion of the reaction, the reaction mixture may be filtered and is stripped of volatiles by heating for about one-half hour to three hours at 80° C. to 110° C. under less than 10 mm. of mercury. If desired, a solvent inert to the reaction may be employed.

The amounts of reactants employed may vary. Generally, however, a mole ratio of polyether polyol to anhydride of from 1:0.1 to 1:8, preferably from 1:0.3 to 1:6, will be employed. The amount of alkylene oxide employed will be such to reduce the acid number of the product to five or less, preferably one or less. The acid number is generally given in units of milligrams of potassium hydroxide per gram. The hydroxyl number of the polyether-ester polyol will vary considerably. Generally, however, the polyols will have a hydroxyl number of from about 20 to 600, preferably from about 25 to 400.

In addition to being useful in the preparation of polyurethanes, the polyols prepared in accordance with the process of the subject invention find utility as precursors in the preparation of graft copolymer dispersions as discussed in U.S. Pat. No. 3,652,639 and U.S. Reissue Pat. No. 29,014.

The following Examples illustrate the invention. All parts are by weight unless otherwise indicated.

EXAMPLE I

A reaction vessel equipped with a thermometer, stirrer, nitrogen source, inlet means and heat exchange means was charged with 73.5 parts (0.75 mole) of maleic anhydride, 0.5 part (100 ppm) of triethylamine and 5050 parts (0.75 mole) of a 2240 equivalent weight polyol prepared by capping with ethylene oxide a propylene oxide adduct of trimethylolpropane, said polyol having an oxyethylene content of fifteen percent by weight of the polyol and a hydroxyl number of 25. The charge was purged with nitrogen, heated to 150° C. and pressurized to 40 psig of nitrogen. Thereafter, 198 parts (4.5 moles) of ethylene oxide was added to the charge at 150° C. for a period of two hours. The reaction temperature was maintained at 150° C. for three hours. A sample taken at this time showed that the acid number of the product was 0.02 indicating that the reaction was complete. The product had a hydroxyl number of 25, a Brookfield visocosity at 25° C. of 2100 cps and a Gardner color rating of 3-4.

The above procedure was duplicated with the exception that no catalyst was employed. A reaction period of about 19 hours was necessary to obtain a product having an acid number of 0.09, a Brookfield viscosity at 25° C. of 2400 cps and a Gardner color rating of 4.

The above procedure was also duplicated with the exception that sodium acetate was substituted for the triethylamine catalyst. While the reaction period was similar, the resulting product had a Brookfield viscosity at 25° C. of 8400 cps and a Gardner color rating of 11-12.

EXAMPLE II

A reaction vessel equiped as described in Example I was charged with 73.5 parts (0.75 mole) of maleic anhydride, 0.25 part (50 ppm) of triethylamine and 5050 parts (0.75 mole) of a 2240 equivalent weight polyol prepared by capping with ethylene oxide a propylene oxide adduct of trimethylolpropane, said polyol having an oxyethylene content of fifteen percent by weight of the polyol and a hydroxyl number of 25. The charge was purged with nitrogen, heated to 150° C. and pressurized to 40 psig of nitrogen. Thereafter, 198 parts (4.5 moles) of ethylene oxide was added to the charge at 150° C. for two hours. The reaction temperature was maintained at 150° C. for three hours. A sample taken at this time showed that the acid number of the product was 0.11 indicating that the reaction was complete. The product had a hydroxyl number of 24.8, a Brookfield viscosity at 25° C. of 2480 cps and a Gardner color rating of 4.

EXAMPLE III

A reaction vessel equipped as described in Example I was charged with 98.0 parts (1.0 mole) of maleic anhydride, 0.48 part (100 ppm) of triethylamine and 4800 parts (1.0) mole of a 1600 equivalent weight polyol prepared by capping, with ethylene oxide a propylene oxide adduct of glycerol, said polyol having an oxyethylene content of thirteen percent by weight of the polyol and a hydroxyl number of about 35. The charge was purged with nitrogen, heated to 150° C. and pressurized to 40 psig of nitrogen. Thereafter, 198 parts (4.5 moles) of ethylene oxide was added to the charge at 150° C. for a period of two hours. The reaction temperature was maintained at 150° C. for four hours, cooled to 30° C. and discharged from the reactor. The resulting product had an acid number of 0.12, a hydroxyl number of 29.9, a Brookfield viscosity at 25° C. of 1428 cps and a Gardner color rating of 4.

This Example was duplicated with the single exception that 9.6 parts of triethylamine was employed (2000 ppm). The resulting product had no measurable acid number, a hydroxyl number of 28.4, a Brookfield viscosity at 25° C. of 2284 cps and a Gardner color rating of 13.

The embodiments of the invention in which an exclusive property or privilege is claimed are defined as follows:

1. In a process for the preparation of polyetherester polyols by the reaction of a polyether polyol and a polycarboxylic acid anhydride to form a half acid-ester followed by the reaction of the half acid-ester with an alkylene oxide to obtain a product having an acid number of 5 mg KOH/gm or less the improvement which comprises carrying out the reaction between the alkylene oxide and the half acid-ester in the presence of from 50–100 ppm based on the weight of the starting polyether polyol of a trialkylamine having from 2 to 4 carbon atoms in the alkyl chain.

2. The process of claim 1 wherein the trialkylamine is triethylamine.

3. The process of claim 1 wherein the polyether polyol is obtained by the reaction of a mixture of ethylene oxide and propylene oxide with a polyhydric alcohol.

4. The process of claim 1 wherein the polycarboxylic acid anhydride is maleic anhydride.

5. The process of claim 1 wherein the alkylene oxide is ethylene oxide.

6. The process of claim 1 wherein the alkylene oxide is propylene oxide.

* * * * *